United States Patent
Greene et al.

(10) Patent No.: US 10,613,103 B2
(45) Date of Patent: Apr. 7, 2020

(54) METHODS OF IDENTIFYING AND TREATING PREMATURE INFANTS AT RISK FOR BPD

(71) Applicant: Mallinckrodt Hospital Products IP Limited, Dublin (IE)

(72) Inventors: Douglas Stuart Greene, Newtown, PA (US); Joseph J. Medicis, Syracuse, NY (US); Jim Potenziano, Binghamton, NY (US)

(73) Assignee: Mallinckrodt Hospital Products IP Limited, Dublin (IE)

( * ) Notice: Subject to any disclaimer, the term of this patent is extended or adjusted under 35 U.S.C. 154(b) by 0 days.

(21) Appl. No.: 15/320,635

(22) PCT Filed: Jun. 18, 2015

(86) PCT No.: PCT/US2015/036413
§ 371 (c)(1),
(2) Date: Dec. 20, 2016

(87) PCT Pub. No.: WO2015/195903
PCT Pub. Date: Dec. 23, 2015

(65) Prior Publication Data
US 2017/0212133 A1 Jul. 27, 2017

Related U.S. Application Data

(60) Provisional application No. 62/014,817, filed on Jun. 20, 2014.

(51) Int. Cl.
| | |
|---|---|
| *A61K 33/00* | (2006.01) |
| *G01N 33/84* | (2006.01) |
| *C12Q 1/6883* | (2018.01) |
| *A61K 9/00* | (2006.01) |
| *G01N 33/497* | (2006.01) |

(52) U.S. Cl.
CPC ............ *G01N 33/84* (2013.01); *A61K 9/007* (2013.01); *A61K 33/00* (2013.01); *C12Q 1/6883* (2013.01); *G01N 33/497* (2013.01); *C12Q 2600/106* (2013.01); *C12Q 2600/156* (2013.01); *G01N 2800/12* (2013.01)

(58) Field of Classification Search
None
See application file for complete search history.

(56) References Cited

U.S. PATENT DOCUMENTS

2012/0093948 A1* 4/2012 Fine ..................... A61M 16/10
424/718
2014/0373836 A1 12/2014 Potenziano et al.

OTHER PUBLICATIONS

Ibrahim, Y. I,; Ninnis, J. R.; Hopper, A. O.; Deming, D. D.; Zhang, A. X.; Herring, J. L.et al. Inhaled Nitric Oxide Therapy Increases Blood Nitrite, Nitrate, and S-Nitrosohemoglobin Concentrations in Infatns with Pulmonary Hypertension. The Journal of Pediatrics, vol. 160, 2, p. 245-251. (Year: 2012).*
Balasubramaniam et al, Mild hypoxia impairs alveolarization in the endothelial nitric oxide synthase-deficient mouse, Am. J. Physiol. Lung Cell Mol. Physiol., 2003, pp. L964-L971, vol. 284.
Ballard et al, Inhaled Nitric Oxide in Preterm Infants Undergoing Mechanical Ventilation,The New England Journal of Medicine, 2006, pp. 343-353, vol. 355, No. 4.
International Search Report for PCT/US2015/036413 dated Dec. 23, 2015, 4 pages.
Schreiber et al, Inhaled Nitric Oxide in Premature Infants with the Respiratory Distress Syndrome, The New England Journal of Medicine, 2003, pp. 2099-2107, vol. 349, No. 22.
Concina, Comparing Diagnostic Criteria for Bronchopulmonary Dysplasia (bpd) of Vermont Oxford Network (von) to the National Institute of Child Health and Development (nichd) Network, Pediatrics, downloaded Nov. 14, 2019 from https://pediatrics.aappublications.org/content/141/1_MeetingAbstract/508, 3 pp.

* cited by examiner

*Primary Examiner* — Jessica Worsham

(57) ABSTRACT

Methods for identifying premature infants at risk for developing bronchopulmonary dysplasia and/or most likely to benefit from administration of inhaled nitric oxide for prevention of bronchopulmonary dysplasia (BPD). Methods for treating premature infants identified as at risk and/or likely to benefit are provided. also provided are methods for identifying premature infants that are not at risk for developing bronchopulmonary dysplasia and/or unlikely to benefit from administration of inhaled nitric oxide for prevention of bronchopulmonary dysplasia, and methods for avoiding risks of toxicity and undesirable side effects associated with inhaled nitric oxide therapy comprising administering only non-iNO treatment modalities to these infants.

7 Claims, No Drawings

METHODS OF IDENTIFYING AND TREATING PREMATURE INFANTS AT RISK FOR BPD

TECHNICAL FIELD

The present invention relates to methods for identifying premature infants most likely to benefit from administration of inhaled nitric oxide for prevention of bronchopulmonary dysplasia (BPD) and methods for treating premature infants so identified.

BACKGROUND

INOMax®, (nitric oxide) (available from Ikaria, Inc. in Hampton, N.J.) for inhalation is an approved drug product for the treatment of term and near-term (<34 weeks gestation) neonates having hypoxic respiratory failure associated with clinical or echocardiographic evidence of pulmonary hypertension (INOmax label SPC-LBL 0303 R 9 herein incorporated by reference).

Data from several animal models indicate that nitric oxide is required for normal lung development. In vivo, nitric oxide is synthesized from L-arginine by a family of nitric oxide synthase (NOS) enzymes. The constitutive isoenzymes endothelial nitric oxide synthase (eNOS) and neuronal nitric oxide synthase (nNOS) mediate nitric oxide in mammals. A cytokine-inducible isoform (iNOS) produces NO as an immune defense mechanism. It has been shown that mice genetically deficient in eNOS are susceptible to mild neonatal hypoxia, with evidence of alveolar simplification and a reduction in vascular volume that is not seen in wild-type mice. (Balasubramaniam et al. (2003) Amer. J. Physiol.—Lung Cellular and Molecular Physiology 284: L964-L971). Administration of inhaled nitric oxide in mice with eNOS deficiency stimulated alveolar and vascular growth.

Survival among preterm infants has improved over time due to improvements in the ability to enhance fetal lung maturation and to manage respiratory distress syndrome. Chronic lung disease, i.e., bronchopulmonary dysplasia (BPD), is now the most significant long-term pulmonary complication. BPD required prolonged hospitalization and is associated with long-term pulmonary and neurodevelopmental problems. In its more severe form, BPD is associated with inflammation, pulmonary hypertension and increased airway resistance, and abnormalities in lung development.

Inhaled nitric oxide (iNO) has been used as a therapy for pulmonary hypertension in full-term infants, but its efficacy for prevention of BPD in premature infants is not clearly established. Published studies report both a benefit (i.e. decreased incidence of BPD) and a lack of such benefit. These studies differ substantially in the preterm infant patient populations studied, the treatment protocols, and determination of outcome. Such mixed results suggest that the therapeutic response is variable due variations in the patient population. The factors contributing to this variability have not been identified and are not understood. There is therefore a need for methods for identifying a subpopulation of premature infants at risk for developing BPD that is more likely to have a therapeutic response to iNO, as evidenced by prevention of long term pulmonary complications such as BPD. Identifying this subpopulation may also avoid administration of iNO to a subpopulation not likely to develop BPD. The present invention addresses this need.

SUMMARY

INOMax®, (nitric oxide) for inhalation is an approved drug product. INOMax is a vasodilator, which, in conjunction with ventilator support of other appropriate agents, is indicated for the treatment of term and near-term (<34 weeks gestation) neonates with hypoxic respiratory failure associated with clinical or echocardiographic evidence of pulmonary hypertension, where it improves oxygenation and reduces the need for extracorporeal membrane oxygenation. The recommended dose of INOmax for the approved indication is 20 ppm, maintained for up to 14 days or until the underlying oxygen desaturation has resolved. Weaning should occur gradually. Adverse reactions per the label include methemoglobinemia and NO2 levels, both which can be dose dependent. The most common adverse reaction is hypotension.

iNO may be administered via the INOMax DSIR®, INOmax® DS or INOvent® delivery systems which deliver operator-determined concentrations of NO in conjunction with a ventilator or breathing gas administration system after dilution with an oxygen/air mixture. A NO delivery system includes a NO administration apparatus, a nitrix oxide gas analyzer and a nitrogen dioxide gas analyzer. Failure to calibrate the NO delivery system could result in under or over dosing of iNO. All delivery systems should be operated by a trained professional.

To ensure safe and effective administration of INOmax to avoid adverse events associated with nitric oxide or $NO_2$, administration of INOmax should only be performed by a health care professional who has completed and maintained training on the safe and effective use of a Nitric Oxide Delivery System provided by the manufacturer of the delivery system and the drug.

INOmax is contraindicated in the treatment of neonates known to be dependent on right-to-left shunting of blood. Warning and precautions includes rebound pulmonary hypertension syndrome following abrupt discontinuation. It is recommended to wean from INOmax as provided in the label. Abrupt discontinuation of INOmax may lead to worsening oxygenation and increasing pulmonary artery pressure, i.e., Rebound Pulmonary Hypertension Syndrome. Signs and symptoms of Rebound Pulmonary Hypertension Syndrome include hypoxemia, systemic hypotension, bradycardia, and decreased cardiac output. If Rebound Pulmonary Hypertension occurs, reinstate INOmax therapy immediately.

Hypoxemia from Methemoglobinemia should also be considered. Nitric oxide combines with hemoglobin to form methemoglobin, which does not transport oxygen. Methemoglobin levels increase with the dose of INOmax; it can take 8 hours or more before steady-state methemoglobin levels are attained. Monitor methemoglobin and adjust the dose of INOmax to optimize oxygenation.

If methemoglobin levels do not resolve with decrease in dose or discontinuation of INOmax, additional therapy may be warranted to treat methemoglobinemia (see INOmax label).

Additionally, nitrogen dioxide ($NO_2$) forms in gas mixtures containing NO and $O_2$. Nitrogen dioxide may cause airway inflammation and damage to lung tissues. If the concentration of $NO_2$ in the breathing circuit exceeds 0.5 ppm, decrease the dose of INOmax. If there is an unexpected change in $NO_2$ concentration, when measured in the breathing circuit, then the delivery system should be assessed in accordance with the Nitric Oxide Delivery System O&M Manual troubleshooting section, and the $NO_2$ analyzer should be recalibrated. The dose of INOmax and/or $FiO_2$ should be adjusted as appropriate.

Other warning and precautions relation to heart failure. Patients with left ventricular dysfunction treated with INOmax may experience pulmonary edema, increased pulmonary capillary wedge pressure, worsening of left ventricular dysfunction, systemic hypotension, bradycardia and cardiac arrest. Discontinue INOmax while providing symptomatic care.

According to the INOmax label, no formal drug-interaction studies have been performed, and a clinically significant interaction with other medications used in the treatment of hypoxic respiratory failure cannot be excluded based on the available data. INOmax has been administered with dopamine, dobutamine, steroids, surfactant, and high-frequency ventilation. Although there are no study data to evaluate the possibility, nitric oxide donor compounds, including sodium nitroprusside and nitroglycerin, may have an additive effect with INOmax on the risk of developing methemoglobinemia. An association between prilocaine and an increased risk of methemoglobinemia, particularly in infants, has specifically been described in a literature case report. This risk is present whether the drugs are administered as oral, parenteral, or topical formulations.

Because clinical trials are conducted under widely varying conditions, adverse reaction rates observed in the clinical trials of a drug cannot be directly compared to rates in the clinical trials of another drug and may not reflect the rates observed in practice. The adverse reaction information from the clinical studies does, however, provide a basis for identifying the adverse events that appear to be related to drug use and for approximating rates.

Certain risk calculators may be used to assist in identifying if a patient is likely to develop BPD. Risk calculator software may take an infant's gestational age, weight and ventilator support needs, among other factors, into account. Such risk calculator may help a clinician or therapist to assist in determining if a premature infant is at risk of developing BPD. The present invention identifies more concise and accurate method for identifying if premature infant is at a risk of developing BPD and then administering iNO to a premature infant at said risk.

In one aspect the invention is directed to methods for identifying premature infants that are at risk for developing BPD and/or are likely to have a therapeutic response to treatment with inhaled nitric oxide (iNO). The methods comprise measuring the concentration of a nitric oxide metabolite in the plasma of the infant prior to initiation of iNO therapy, wherein a concentration of the metabolite that is lower than a normal concentration of the metabolite indicates that the infant is at risk for developing BPD and/or is likely to have a therapeutic response to treatment with iNO for prevention of BPD. In certain embodiments, the nitric oxide metabolite concentration is a concentration of nitrite, nitrate, or both. In further embodiments, a total concentration of nitrite and nitrate of less than about 50 μM indicates that the infant is at risk for developing BPD and/or is likely to have a therapeutic response to treatment with iNO for prevention of BPD. This includes, in certain embodiments, instances in which the total nitrite and nitrate concentration in the plasma is below the limits of detection in the assay. In a specific embodiment, a total concentration of nitrite and nitrate of about 0-45 μM, about 5-40 μM, about 10-30 μM, about 20 μM, or below the detection limit of the assay (i.e., effectively 0) indicates that the infant is at risk for developing BPD and/or is likely to have a therapeutic response to treatment with iNO. In other embodiments, a total concentration of nitrite and nitrate of at least about 50 μM indicates that the infant is not at risk for developing BPD and/or is unlikely to have a therapeutic response to treatment with iNO. In a specific embodiment, a total concentration of nitrite and nitrate of greater than about 60 μM, or about 60-185 μM, indicates that the infant is not at risk for developing BPD and/or is unlikely to have a therapeutic response to treatment with iNO. Experimental data from a clinical trial show that the predictive accuracy for therapeutic efficacy of iNO administration is about 75% when iNO is administered to a premature infant at risk for BPD when the total plasma concentration of nitrate and nitrite of the infant is less than about 50 μM, about 0-45 μM, about 5-40 μM, about 10-30 μM, about 20 μM, or below the detection limits of the assay. Experimental data from the clinical trial also show that the predictive accuracy for lack of efficacy of iNO administration is about 56% when the total plasma concentration of nitrate and nitrite in the plasma of the premature infant is at least about 50 μM, at least about 60 μM, or about 60-185 μM.

In a second aspect the invention is directed to methods for identifying premature infants that are at risk for developing BPD and/or are likely to have a therapeutic response to treatment with iNO, the methods comprising measuring the concentration of nitric oxide (NO) in air exhaled by the infant prior to initiation of iNO therapy, wherein a concentration of NO that is lower than a normal concentration of NO (i.e., lower than 2.5 ppb) indicates that the infant is at risk for developing BPD and/or is likely to have a therapeutic response to treatment with iNO for prevention of BPD. In certain embodiments, a concentration of NO in exhaled air that ranges from about 0.5-1.5 ppb indicates that the infant is at risk and/or is likely to have a therapeutic response to treatment with iNO. In a specific embodiment, a concentration of NO in exhaled air that is about 1.5 ppb or less, about 1 ppb or less, or ranges from about 0.5-0.9 ppb, indicates that the infant is at risk and/or is likely to have a therapeutic response to treatment with iNO. In other embodiments, a concentration of NO in air exhaled by the infant prior to initiation of iNO therapy that is normal or higher than a normal concentration of NO (i.e., about 2.5 ppb or higher) indicates that the infant is not at risk for developing BPD and/or is unlikely to have a therapeutic response to treatment with iNO.

In a third aspect the invention is directed to methods for identifying premature infants that are at risk for developing BPD and/or are likely to have a therapeutic response to treatment with iNO, the methods comprising obtaining a blood or tissue sample from the infant prior to initiation of iNO therapy, and analyzing the blood, tissue, or other sample for a mutation in a gene encoding a nitric oxide synthase (eNOS, nNOS or iNOS) that results in decreased endogenous synthesis of nitric oxide, wherein the presence of the mutation indicates that the infant is at risk for developing BPD and/or is likely to have a therapeutic response to treatment with iNO. In certain embodiments, detection of a T-786C mutation or a $Glu^{298} \rightarrow Asp$ polymorphism (G894T mutation) in the eNOS gene indicates that the infant is at risk and/or is likely to have a therapeutic response to treatment with iNO. In other embodiments, absence of a mutation in a gene encoding a nitric oxide synthase, indicating unimpaired enzyme activity and normal endogenous synthesis of nitric oxide, indicates that the infant may not be at risk for developing BPD and/or may be unlikely to have a therapeutic response to treatment with iNO.

In a further aspect the invention is directed to methods for treating premature infants at risk for developing BPD with iNO to prevent BPD, the methods comprising identifying a premature infant that is at risk for developing BPD and is likely to have a therapeutic response to treatment with iNO using any of the foregoing identification methods, and administering iNO to the infant. In an alternative embodiment, the invention is directed to methods for avoiding risks associated with administration of iNO to premature infants at risk for developing BPD or for prevention of BPD, the methods comprising identifying a premature infant that is not at risk for developing BPD and/or is unlikely to have a therapeutic response to treatment with iNO using any of the foregoing identification methods, and treating the infant with one or more modalities for prevention of BPD that do not include iNO. In certain embodiments, the premature infant that is at risk or not at risk for developing BPD, and/or is likely or unlikely to have a therapeutic response to treatment with iNO is identified immediately after birth, on the day of birth, before the third day after birth, or before the fifth day after birth. In certain embodiments the infant likely to have a therapeutic response is treated with iNO beginning at least five days after birth, or five to fourteen days after birth. In specific embodiments, treatment begins five to 10 days after birth, or 5 to 7 days after birth. In further embodiments, treatment of a premature infant identified as at risk for developing BPD and/or is likely to have a therapeutic response to treatment with iNO comprises administering decreasing concentrations of NO, beginning at 20 ppm. In certain embodiments, the initial dose of 20 ppm NO is decreased to 10, 5 and 2 ppm over the course of administration. In specific embodiments, the administration of NO is for about 20-30 days, preferably a minimum of at least 24 days. In a specific example of NO administration, the initial administration of 20 ppm NO is for 48 to 96 hours, followed by 10 ppm 5, ppm and 2 ppm at weekly intervals.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

It has been discovered that certain biomarkers present in premature infants are predictive of the risk of developing BPD and/or the likelihood of a therapeutic response to iNO to prevent BPD. As used herein, the term "therapeutic response to iNO" means that iNO administration increases the rate of survival without bronchopulmonary dysplasia (BPD) at 36 weeks of post menstrual age compared to the rate of survival with development of BPD at 36 weeks of post menstrual age in an untreated premature infant population. As used herein, the term "premature infant", "preterm infant" and the like means infants born at less than 30 weeks gestational age. The biomarkers identified are of three types: a) the concentration of metabolites of NO, such as nitrite and nitrate, in blood or plasma, b) the concentration of NO in exhaled air, and c) the presence or absence of a mutation in the eNOS gene that decreases endogenous NO production, or any combination thereof.

A first method for identifying premature infants that are at risk for developing BPD and/or are likely to have a therapeutic response to treatment with iNO comprises measuring the concentration of one or more nitric oxide metabolites in the plasma of the infant prior to iNO therapy, wherein a concentration of the metabolite that is lower than a normal concentration of the metabolite prior to treatment with iNO indicates that the infant is at risk and/or is likely to have a therapeutic response to treatment with iNO. A modification of the first method may be used for identifying premature infants that are not at risk for developing BPD and/or are unlikely to have a therapeutic response to treatment with iNO, so that non-iNO treatment modalities may be administered and the risks of toxicity and undesirable side effects of iNO therapy can be reduced. In this modification, if a concentration of the metabolite is normal or higher than a normal concentration of the metabolite prior to treatment with iNO, iNO is not administered. Typically, in such cases only non-iNO treatment modalities will be administered for prevention of BPD. By way of example, the metabolite that is measured is nitrite and/or nitrate.

Several suitable tests are available for quantitating nitrite and/or nitrate in plasma. For example, the Nitrate/Nitrite Colorimetric Assay Kit (Cayman Chemical Company, Ann Arbor, Mich.), the Nitrate/Nitrite Assay (Kamiya Biomedical Company, Seattle, Wash.), and the Total Nitric Oxide and Nitrate/Nitrite Parameter Assay Kit (R&D Systems) are all suitable for use in the invention as instructed by the manufacturer. It has been found that a total concentration of nitrite and nitrate in plasma of about 50 µM or more correlates with reduced risk of developing BPD and with non-responsiveness to iNO therapy. A total concentration of nitrite and nitrate of less than about 50 µM, including concentrations that are below the limit of detection in the assay used (effectively 0), indicates that the premature infant is at risk for developing BPD and/or is likely to have a therapeutic response to treatment with iNO. In specific examples, the total concentration of nitrate and nitrite from about 0-45 µM, about 5-40 µM, about 10-40 µM, about 10-30 µM, about 20 µM, or below the detection limit of the assay indicates that the infant is at risk for developing BPD and/or is likely to have a therapeutic response to treatment with iNO. In specific examples, a total concentration of nitrate and nitrite at least about 50 µM, greater than about 60 µM, or about 60-185 µM, indicates that the infant is not at risk for developing BPD and/or is unlikely to have a therapeutic response to treatment with iNO.

A second method for identifying premature infants that are likely to have a therapeutic response to iNO therapy comprises measuring the concentration of NO in exhaled air while the infant breathes ambient air or air having all naturally-occurring NO removed. The measurement of NO concentration in exhaled air is taken prior to treatment with iNO. If the concentration of NO in air exhaled by the infant is lower than a normal concentration of exhaled NO, the infant is at risk for developing BPD and/or is likely to have a therapeutic response to iNO treatment for prevention of BPD. Typically, healthy pre-term infants exhale about 2.5 ppb of NO when breathing ambient air. However, concentrations of NO in exhaled air from about 0.5-1.5 ppb indicate that the infant is at risk for developing BPD and/or is likely to have a therapeutic response to iNO administration. In a particular embodiment a concentration of exhaled NO that is about 1.5 ppb or less, about 1 ppb or less, for example 0.5-0.9 ppb, indicates that the infant is at risk and/or is likely to have a therapeutic response to iNO administration. A modification of the second method may be used for identifying premature infants that are not at risk for developing BPD and/or are unlikely to have a therapeutic response to treatment with iNO, so that non-iNO treatment modalities may be administered and the risks of toxicity and undesirable side effects of iNO therapy can be reduced. In this modification, if a concentration of NO in exhaled air is normal or higher than a normal concentration of NO prior to treatment with iNO (about 2.5 ppm or above), iNO is not administered. Typically, in such cases only non-iNO treatment modalities for prevention of BPD will be administered.

Several suitable instruments and devices are available for measuring the concentration of NO in exhaled air, and can be adapted for use with preterm infants. The analytical instrument should have a sensitivity for gas samples of at least 0.5 ppb and a range of at least 0.5-5 ppb. For example, exhaled breath samples may be analyzed using the Sievers Nitric Oxide Analyzer (NOA 280i) (GE Analytical Instruments, Boulder, Colo.).

A third method for identifying premature infants that are at risk for developing BPD and/or are likely to have a therapeutic response to iNO administration comprises, prior to initiation of iNO therapy, analyzing a blood, plasma, serum, orally component of blood, plasma or serum, tissue, or other sample, tracheal aspirates or the like, for the presence of a mutation in a gene encoding a nitric oxide synthase (e.g., eNOS, nNOS or iNOS), wherein the mutation results in decreased endogenous synthesis of nitric oxide. Any known mutation or genetic anomaly in a nitric oxide synthase gene can be analyzed, provided it results in decreased endogenous synthesis of nitric oxide. Examples of mutations suitable for analysis include the T-786C mutation (a T→C mutation at position −786 in the 5' flanking region of the eNOS gene) and G894T (a G→T mutation at position 894 of the eNOS coding sequence that results in a $Glu^{298}$→Asp polymorphism in the enzyme). Testing for the T-786C mutation is commercially available through diagnostic laboratories such as Molecular Diagnostics Laboratories (MDL, Covington, Ky.). In addition, any of the known laboratory methods for analysis of single nucleotide polymorphisms (SNPs), insertions, deletions and genotyping is suitable for use in the invention, e.g., melting curve analysis of polymerase chain reaction products or polymerase chain reaction-restriction fragment length polymorphism analysis. A modification of the third method may be used for identifying premature infants that are not at risk for developing BPD and/or are unlikely to have a therapeutic response to treatment with iNO, so that non-iNO treatment modalities may be administered and the risks of toxicity and undesirable side effects of iNO therapy can be reduced. In this modification, if no mutation that reduced endogenous synthesis of nitric oxide is detected in a gene encoding a nitric oxide synthase, endogenous synthesis of nitric oxide will be normal and iNO is not administered. Typically, in such cases only non-iNO treatment modalities for prevention of BPD will be administered.

The absence of a mutation in a gene encoding a nitric oxide synthase that results in reduced endogenous synthesis of nitric oxide (indicating normal NOS activity) correlates with reduced risk of developing BPD and/or with a failure of therapeutic response to treatment with iNO for prevention of BPD. The presence of a mutation that reduces endogenous synthesis of nitric oxide due to impairment of NOS activity indicates that the infant is at risk for developing BPD and/or is likely to have a therapeutic response to iNO treatment.

Any of the foregoing methods for identifying premature infants that are at risk for developing BPD and/or are likely to have a therapeutic response to iNO therapy for prevention of BPD can be used in connection with methods for preventing BPD in premature infants. In these methods, prior to initiation of iNO therapy, premature infants requiring mechanical ventilation are evaluated as discussed above for concentrations of nitric oxide metabolites in their plasma, concentrations of exhaled nitric oxide while breathing ambient air or air from which substantially all naturally-occurring nitric oxide has been removed, and/or a mutation in a gene encoding NOS that results in decreased endogenous synthesis of nitric oxide. If the result of one or more of the tests indicates that the infant is at risk for developing BPD and is likely to have a therapeutic response to iNO administration, iNO therapy is initiated. Typically, if one or more of the tests indicates that the infant is not at risk and/or is unlikely to have a therapeutic response to iNO administration, administration of iNO will be avoided and the infant may be treated only with one or more non-iNO modalities for prevention of BPD. These identification tests provide improved information for weighing the risk vs. benefit of treating the infant with iNO, thereby reducing the risk of toxicity and undesirable side effects of the treatment. In addition, the identification tests substantially increase the likelihood of efficacy of iNO treatment for the individual premature infant.

Any treatment protocol known in the art for administering iNO to premature infants to prevent BPD is suitable for use in the present invention, after determining that the infant is at risk for developing BPD and/or is likely to have a therapeutic response to iNO administration. Generally, one or more of the tests to identify the premature infant that is at risk and/or is likely to have a therapeutic response to administration of iNO are performed from birth to about 14 days after birth. In certain embodiments, the one or more tests are performed between birth and about 5 days after birth. In specific embodiments, the one or more tests are performed immediately after birth, on the day of birth, before the third day after birth, or before the fifth day after birth.

It has been reported that on the third day after birth there is no difference in exhaled NO in premature infants that subsequently develop BPD and those that do not. Accordingly, particularly for evaluation of exhaled NO, the evaluation is generally performed at a time between birth and the third day after birth to obtain the most accurate results.

In general, administration of iNO to premature infants that have been identified as at risk for developing BPD and/or as likely to have a therapeutic response begins at least five days after birth. Treatment of these infants may begin 5 to 14 days after birth, 7 to 21 days after birth, or 5 to 7 days after birth. Administration of iNO generally continues for 20-30 days after it is initiated. In specific treatment protocols, administration of iNO may be continued for at least 24 days, For example, the protocol disclosed by R. A. Ballard, et al. (2006. *N. Eng. J. Med.* 355:343-353) is a particularly useful treatment method. In this study, premature infants between 7 and 21 days of age requiring ventilator support and at risk for developing BPD received decreasing concentrations of nitric oxide, beginning at 20 ppm, for a minimum of 24 days. The initial dose of nitric oxide was administered for 48-96 hours, and subsequent doses of 10, 5, and 2 ppm were administered at weekly intervals thereafter. The authors report that administration of iNO according to this protocol improves the pulmonary outcome for premature infants who are at risk for BPD with no apparent short term adverse effects.

A further example of a suitable administration protocol is that of M. D. Schreiber, et al. (2003. *N. Engl. J. Med.* 349:2099-2107), in which premature infants undergoing mechanical ventilation for respiratory distress syndrome were treated with iNO at 10 ppm on day 1, followed by 5 ppm for six days.

EXAMPLES

A multi-center, double blind, placebo-controlled randomized clinical trial was conducted to examine the efficacy of iNO in preterm infants less than 30 weeks gestational age and less than 1250 grams who required mechanical ventilation or positive pressure support on days 5 to 14 after birth. A secondary objective of the trial was to examine the pharmacokinetics (PK) of nitric oxide in preterm infants using plasma nitrite and nitrate (NOx) as surrogate biomarkers. Continuous iNO administration was begun at 20 ppm by administration into the inspiratory limb of the ventilator circuit in the mechanically ventilated subject using an INOvent® delivery device. Therapy was continued for 24 days, following a dose reduction schedule (10 ppm after 72 hours of treatment, 5 ppm on day 10). If an infant was extubated before 24 days, therapy was continued via nasal continuous positive airway pressure or nasal cannula to complete the protocol.

Because of the challenge to measure free NO in systemic circulation, the PK assessment was done via plasma concentration data of NOx (nitrite and nitrate). In addition, methemoglobin (another metabolite of NO) was used as a secondary variable for PK evaluation. This evaluation was done to understand the relationship between pharmacokinetic behavior of iNO and clinical outcomes. The sampling protocol included pre-treatment time points (less than 2 hours before initiation of NO dosing), as well as a variety of time points during iNO therapy and after discontinuation of iNO therapy.

A liquid chromatographic/mass spectrophotometric (LC/MS) assay method was developed and qualified for measurement NOx in human plasma. The quantitation of NOx was performed using the $^{15}$N-stable isotope labeled nitrate as an internal standard. Nitrate reductase and NADH was added to the samples for enzymatic reduction of nitrate to nitrite in plasma. Upon completion of the reduction reaction, acetone was added to precipitate plasma proteins. The alkylating reagent, pentafluorobenzyl bromide (PFBBr), was subsequently added to the samples to convert nitrite to a chemically stable pentafluorobenzyl derivative. After completion of derivatization, plasma supernatant was injected into the LC/MS for analysis. Plasma concentrations of total nitrite and nitrate were measured and reported as NOx using this assay method. The instrumental analysis of the nitrite and NOx samples was performed using reversed-phase high performance liquid chromatography (HPLC), coupled with mass spectrometric (MS) detection. A triple-quadrupole mass spectrometer was used to acquire single-ion recording (SIR) data, and was operated in the negative electrospray ionization mode for the detection of the nitrite derivative (PFB-NO$_2$) and the $^{15}$N-labeled internal standard derivative.

The NOx results for subjects that had a therapeutic response to iNO treatment are shown in the following Table:

| Subjects who had a response with Nitric Oxide Treatment | | | | | |
|---|---|---|---|---|---|
| Subject | Race | Treatment | Primary Outcome | Lab Test Result | Lab Test Unit |
| 425301 | WHITE | NITRIC OXIDE | Y | <LLOQ | uM |
| 427801 | WHITE | NITRIC OXIDE | Y | <LLOQ | uM |
| 1821202 | BLACK | NITRIC OXIDE | Y | 77.5 | uM |
| 3412801 | WHITE | NITRIC OXIDE | Y | <LLOQ | uM |
| Mean NOx level | | | | 19.4 | uM |

Values <LLOQ (below the limit of quantitation of the assay) were assumed to be zero (0)

The NOx results for subjects that did not have a therapeutic response to iNO treatment are shown in the following Table:

| Subjects who DID NOT have a response with Nitric Oxide Treatment | | | | | |
|---|---|---|---|---|---|
| Subject | Race | Treatment | Primary Outcome | Lab Test Result | Lab Test Unit |
| 203801 | HISPANIC | NITRIC OXIDE | N | 62.3 | uM |
| 414501 | WHITE | NITRIC OXIDE | N | <LLOQ | uM |
| 1110501 | BLACK | NITRIC OXIDE | N | <LLOQ | uM |
| 1623801 | BLACK | NITRIC OXIDE | N | 184 | uM |
| 1816101 | WHITE | NITRIC OXIDE | N | 62.5 | uM |
| 3631502 | WHITE | NITRIC OXIDE | N | <LLOQ | uM |
| 3632801 | HISPANIC | NITRIC OXIDE | N | <LLOQ | uM |
| 3635401 | WHITE | NITRIC OXIDE | N | 76.8 | uM |
| 3917501 | WHITE | NITRIC OXIDE | N | 62.7 | uM |
| Mean NOx Level | | | | 49.8 | uM |

Values <LLOQ (below the limit of quantitation of the assay) were assumed to be zero (0)

As can be seen from the results above, treatment with iNO was not effective in subjects with NOx levels from 62.3 μM to 184 μM. The calculated mean NOx concentration for the non-responding population was 49.8 μM. It can be concluded that a NOx concentration in plasma of about 50 μM or above indicates that the subject is less likely to have a therapeutic response to iNO administration.

Conversely, the results show that treatment was therapeutically effective in subjects having an average NOx concentration of about 20 μM or less. It can be concluded that a NOx concentration in plasma of less than 50 μM, e.g., about 10-30 μM, indicates that the subject is more likely to have a therapeutic response to iNO administration.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A method for reducing the likelihood of a premature infant of developing bronchopulmonary dysplasia comprising:
    a) obtaining a plasma sample from the infant prior to initiation of inhaled nitric oxide therapy;
    b) measuring a total concentration of nitrite and nitrate in the plasma sample;
    c) determining whether the measured concentration of nitrite and nitrate is less than about 50 µM, wherein a concentration of less than about 50 µM indicates that the infant is likely to have a therapeutic response to inhaled nitric oxide; and
    d) treating the infant with inhaled nitric oxide to reduce the likelihood of development of bronchopulmonary dysplasia when the measured concentration of nitrite and nitrate is less than about 50 µM,
    wherein the premature infant is less than 30 weeks gestational age.

2. The method of claim 1, wherein the measured concentration of nitrite and nitrate is about 0-45 µM, about 5-40 µM, about 10-30 µM, about 20 µM, or below the detection limit of an assay used to measure the concentration.

3. A method of reducing the likelihood of a premature infant of developing bronchopulmonary dysplasia comprising:
    a) testing the infant for one or more of
        (i) a plasma total concentration of nitrate and nitrite;
        (ii) a concentration of nitric oxide in exhaled ambient or nitric oxide-free air; and
        (iii) presence of a genetic mutation in a gene encoding nitric oxide synthase that results in decrease endogenous synthesis of nitric oxide;
    b) determining whether the total concentration of nitrate and nitrite in the plasma is less than about 50 µM, whether the concentration of nitric oxide in the exhaled air is less than about 1.5 ppb and/or whether the genetic mutation is present or absent; and
    c) treating the infant with inhaled nitric oxide to reduce the likelihood of development of bronchopulmonary dysplasia if the total concentration of nitrate and nitrite in the plasma is less than about 50 µM, the concentration of nitric oxide in the exhaled air is less than about 1.5 ppb, and/or that the genetic mutation is present,
    wherein the premature infant is less than 30 weeks gestational age.

4. The method of claim 3, wherein the infant is treated with decreasing dosages of inhaled nitric oxide.

5. The method of claim 4, wherein an initial dose of 20 ppm is administered for 48-96 hours, and subsequent doses of 10, 5 and 2 ppm are administered at weekly intervals thereafter.

6. The method of claim 3, wherein treatment is initiated at 5-14 days after birth.

7. The method of claim 3, wherein the infant is treated for 20-30 days.

* * * * *